US010556067B2

(12) United States Patent
Wei

(10) Patent No.: US 10,556,067 B2
(45) Date of Patent: Feb. 11, 2020

(54) AUTOMATIC INJECTION DEVICE FOR MULTIPLE DOSING

(71) Applicant: Min Wei, Carmel, IN (US)

(72) Inventor: Min Wei, Carmel, IN (US)

(73) Assignee: Min Wei, Carmel, IN (US)

( * ) Notice: Subject to any disclaimer, the term of this patent is extended or adjusted under 35 U.S.C. 154(b) by 28 days.

(21) Appl. No.: 15/513,598

(22) PCT Filed: Oct. 7, 2015

(86) PCT No.: PCT/US2015/054436
§ 371 (c)(1),
(2) Date: Mar. 23, 2017

(87) PCT Pub. No.: WO2016/060908
PCT Pub. Date: Apr. 21, 2016

(65) Prior Publication Data
US 2017/0246396 A1 Aug. 31, 2017

Related U.S. Application Data

(60) Provisional application No. 62/062,899, filed on Oct. 12, 2014.

(51) Int. Cl.
*A61M 5/31* (2006.01)
*A61M 5/315* (2006.01)
(Continued)

(52) U.S. Cl.
CPC ........ *A61M 5/3158* (2013.01); *A61M 5/2033* (2013.01); *A61M 5/28* (2013.01);
(Continued)

(58) Field of Classification Search
CPC ...... A61M 2005/31508; A61M 5/2033; A61M 5/28; A61M 5/31501; A61M 5/3158; A61M 5/3202; A61M 5/3243; A61M 5/3287
See application file for complete search history.

(56) References Cited

U.S. PATENT DOCUMENTS 5,480,387 A * 1/1996 Gabriel ................ A61M 5/20
604/134
5,584,815 A * 12/1996 Pawelka ............... A61M 5/19
604/135
(Continued)

FOREIGN PATENT DOCUMENTS

WO WO-2013034647 A1 * 3/2013 ........ A61M 5/31533
WO WO2014080020 * 5/2014 ............. A61M 5/20

*Primary Examiner* — Imani N Hayman
(74) *Attorney, Agent, or Firm* — Min Wei

(57) ABSTRACT

A medical injection device used to deliver multiple doses of medication, including: a medication container having a movable piston; a push rod assembly having a plurality of spaced-apart position settings disposed along the length, the push rod assembly displacing the movable piston to dispense medication from the medication container; a spring to bias the push rod assembly to move toward the distal end of the medical injection device; a releasable restraining member configured to restrain the push rod assembly in a locked state against the biasing of the spring, upon release of the releasable restraining member, the push rod assembly moves toward the distal end of the medical injection device; and an arming mechanism configured to move the push rod assembly toward the proximal end of the medical injection device.

12 Claims, 20 Drawing Sheets

(51) Int. Cl.
*A61M 5/20* (2006.01)
*A61M 5/28* (2006.01)
*A61M 5/32* (2006.01)

(52) U.S. Cl.
CPC ...... *A61M 5/31501* (2013.01); *A61M 5/3202* (2013.01); *A61M 5/3243* (2013.01); *A61M 5/3287* (2013.01); *A61M 5/31553* (2013.01); *A61M 5/31555* (2013.01); *A61M 5/31595* (2013.01); *A61M 5/3204* (2013.01); *A61M 2005/202* (2013.01); *A61M 2005/206* (2013.01); *A61M 2005/31508* (2013.01)

(56) References Cited

U.S. PATENT DOCUMENTS

| | | | | |
|---|---|---|---|---|
| 5,679,111 | A | * 10/1997 | Hjertman | A61M 5/20 604/135 |
| 5,820,602 | A | * 10/1998 | Kovelman | A61M 5/172 604/187 |
| 2002/0107487 | A1 | * 8/2002 | Preuthun | A61M 5/14566 604/218 |
| 2013/0218087 | A1 | * 8/2013 | Davies | A61M 5/2448 604/191 |

* cited by examiner

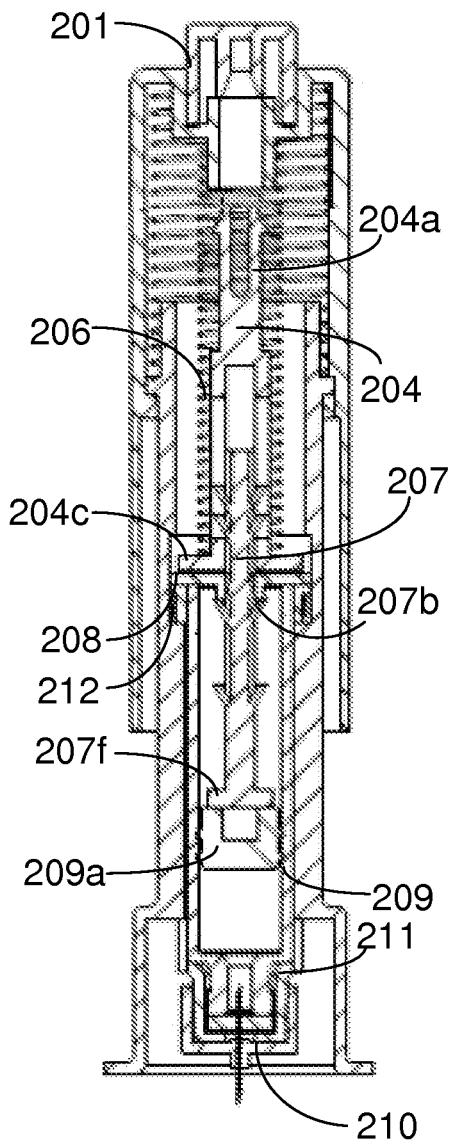
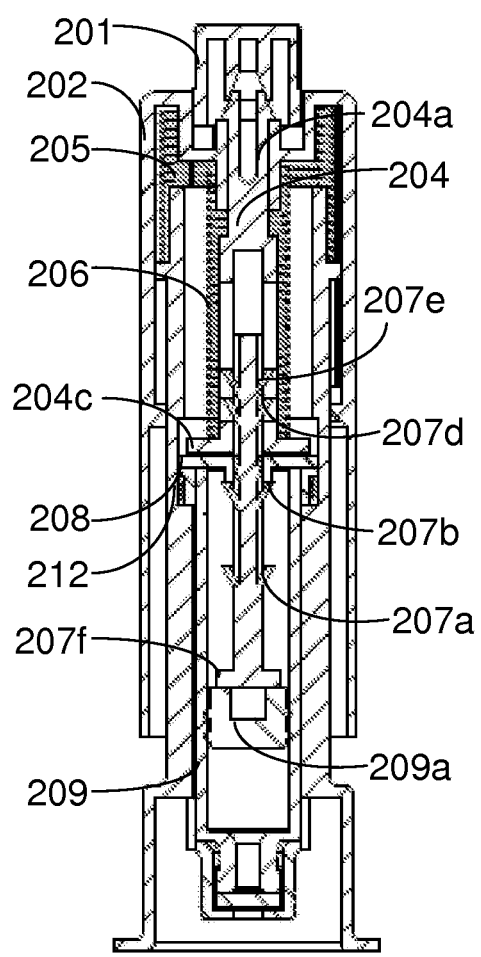
FIG. 21                    FIG. 22

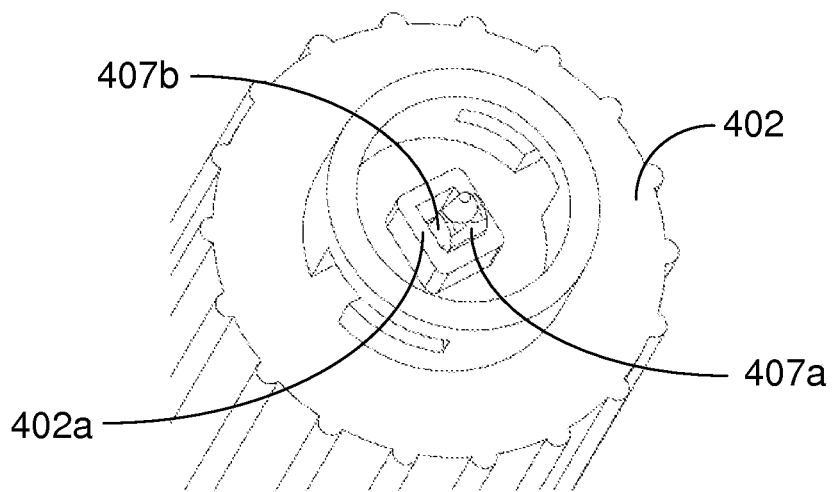
FIG. 35
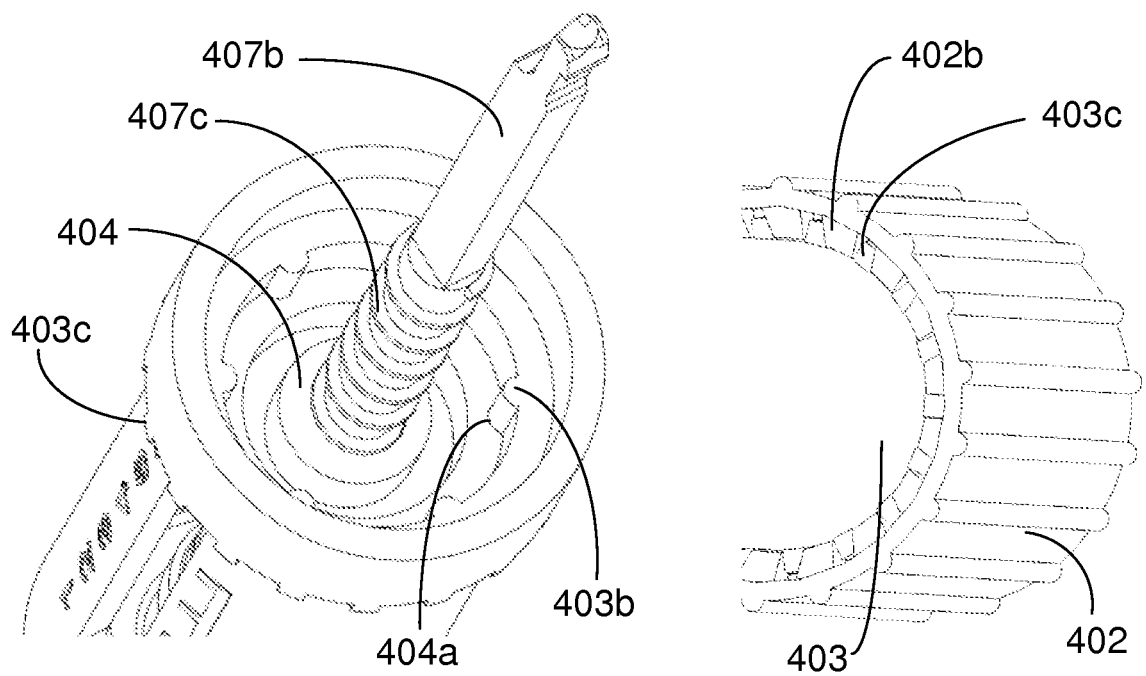
FIG. 36
FIG. 37

AUTOMATIC INJECTION DEVICE FOR MULTIPLE DOSING

TECHNICAL FIELD

The invention relates to an automatic medication injection device for delivering liquid medications.

BACKGROUND OF THE INVENTION

As biologic drugs increase in popularity, parenteral delivery devices are expected to be widely used. Injection drug delivery devices, such like the autoinjector, can ease medication preparation/administration and reduce needle injury, which results in improved patient convenience and compliance. Due to the advantages mentioned above, more patients and healthcare professionals prefer automatic injection devices to the traditional manual syringes. Many devices of the above mentioned type allowing a patient to self-administer one or more (generally two) doses of a medicament are known. U.S. Pat. No. 6,575,939 discloses an autoinjector device comprising a syringe housed in a casing formed by an inner part and an outer part capable of sliding in relation to each other. This autoinjector allows a single dose of medicament to be administered. EP Pat. No. 700307 discloses a two-dose autoinjector allowing the automatic delivering of a first dose of a medicament and the manual administration of a second dose. An autoinjector of this type is commercially available under the trade mark Twinject® and allows the first dose to be administered automatically, but the second dose must be manually administered. U.S. Pat. No. 8,961, 463 describes an auto-injector that allows the end-user to self administer first and second doses of a medicament. However, the actuation mechanism for delivering the first and second doses are quite different and the mechanism cannot be applied for delivering more than two doses.

Another popular type of injection device is a pen injector. Such pen injector devices may contain a dose metering mechanism that administers a dose based on end-user selection. These devices are capable of delivering multiple doses. As for pen injectors, a lead screw or rotating plunger is provided which is mechanically coupled to a dose-setting knob or other actuator through a series of mechanical connections. The typical pen injector mechanism is fairly complex and consists of multiple cooperating parts. The pen injector design mechanism also limits the maximum delivery volume (normally less than 0.5 mL). For the reasons of cost and simplicity of use, a minimum number of working parts is desired.

It would be an improvement in the art, therefore, to provide a multiple use autoinjector for the automatic injection of a medicament, which is user-friendly and is easier to manufacture as compared to the conventional devices.

SUMMARY OF THE INVENTION

The basic idea of the invention is to provide medication delivering mechanisms with features that are typically actuated through direct application of linear force. Dose size is a direct function of advancement of a push rod assembly. Accordingly, it is an aspect of the present invention to provide the push rod assembly for an autoinjector, which may be controllably advanced with a minimum number of cooperating parts.

The present invention provides a reusable, spring-driven autoinjector. The autoinjector of the present invention includes a spring-loaded drive mechanism, a trigger mechanism, and a pre-filled medication container. The body of the autoinjector of the present invention includes proximal and distal portions, with the proximal portion housing the drive mechanism and the distal portion housing the medication container. The drive mechanism includes one or more driving springs in association with a push rod assembly. Advantageously, the present invention are achieved by providing a medical injector including the push rod assembly with a plurality of spaced-apart position setting features along the length thereof. The position setting features are configured to allow the push rod to displace distally toward a distal end of the body but not proximally toward a proximal end of the body. The drive mechanism is also capable of being re-armed for multiple times of injection. In addition, the driving mechanism is further provided for controlling the sliding of the medication container from the armed positions to inject the injection needle in an injection site.

Additional and/or other aspects and advantages of the present invention will be set forth in part in the description that follows and, in part, will be apparent from the description, or may be learned by practice of the invention.

BRIEF DESCRIPTION OF THE DRAWINGS

The figures are schematic and simplified for clarity, and they just show details, which are essential to the understanding of the invention, while other details are left out. Throughout, the same reference numerals are used for identical or corresponding parts.

FIG. 17-24 show the injection and re-arming operations of the first alternative automatic medication injection device assembly according to the invention.

FIG. 35-37 show engagements between components of the third alternative automatic medication injection device assembly according to the invention.

DETAILED DESCRIPTION THE DRAWINGS

Figure 1:
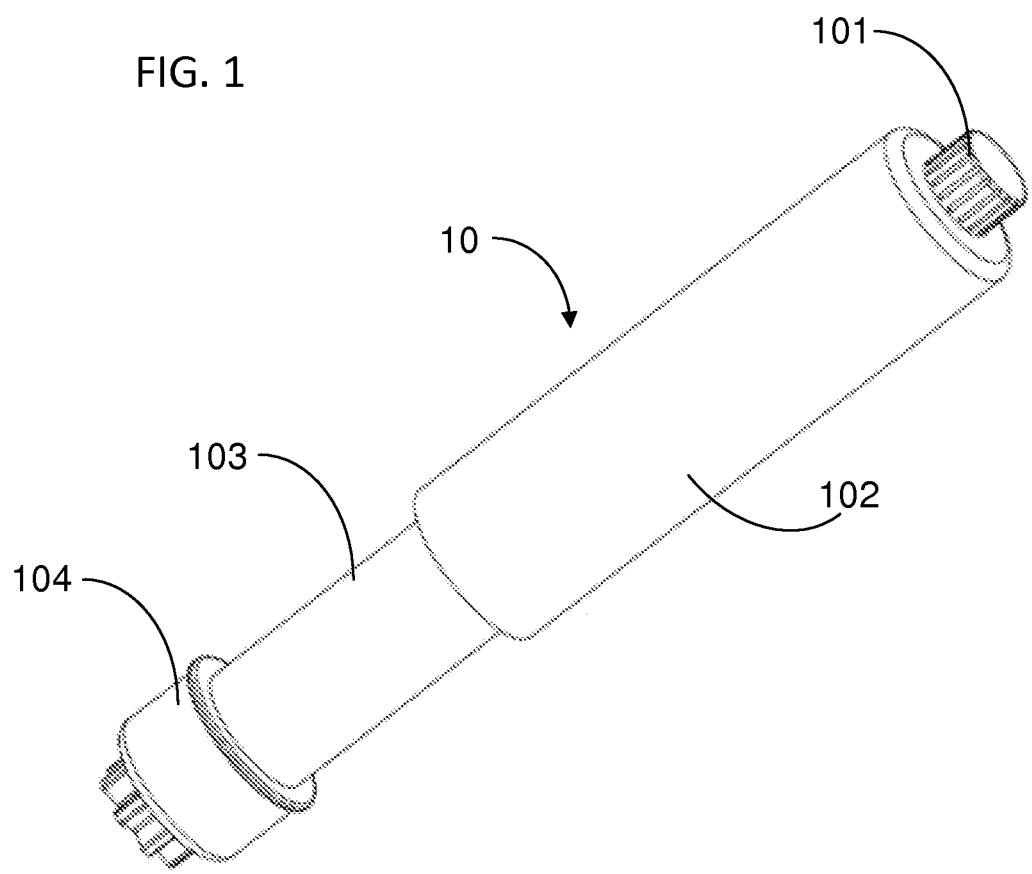
FIG. 1 is a perspective view of an exemplary automatic medication injection device assembly according to the invention.
Figure 2:
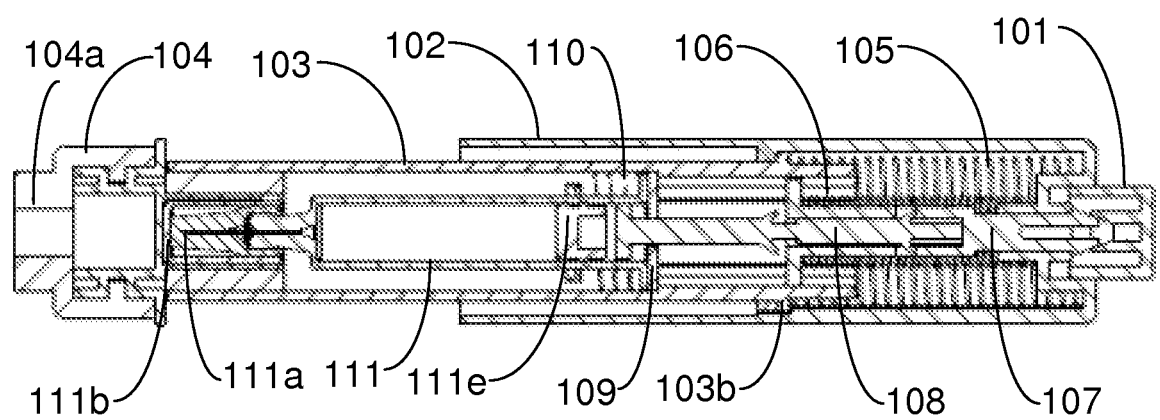
FIG. 2 shows a cross-sectional view of the exemplary automatic medication injection device assembly according to the invention.
Figure 3:
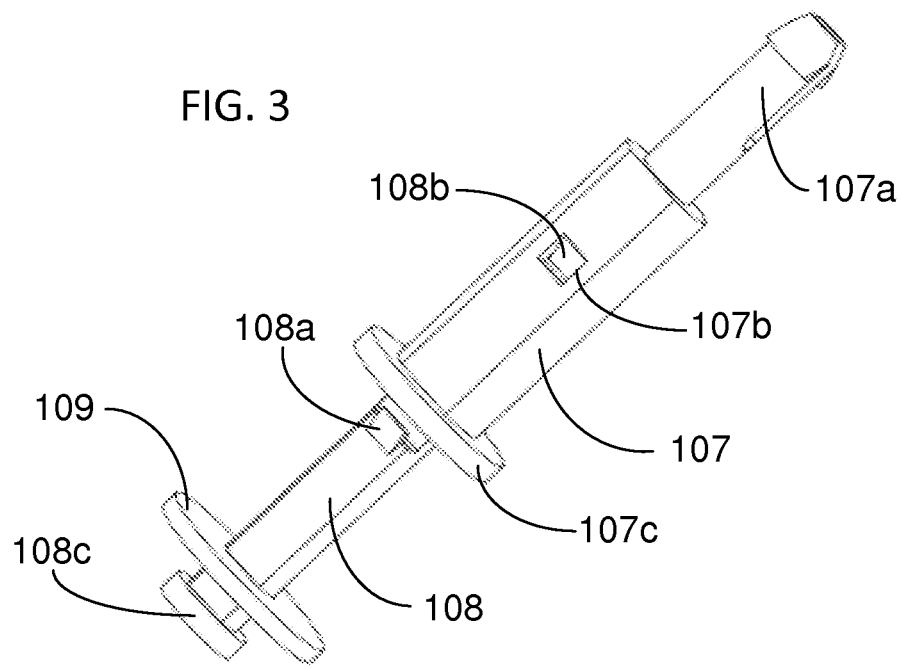
FIGS. 3 and 4 show a push rod assembly of the exemplary automatic medication injection device assembly according to the invention.
Figure 4:
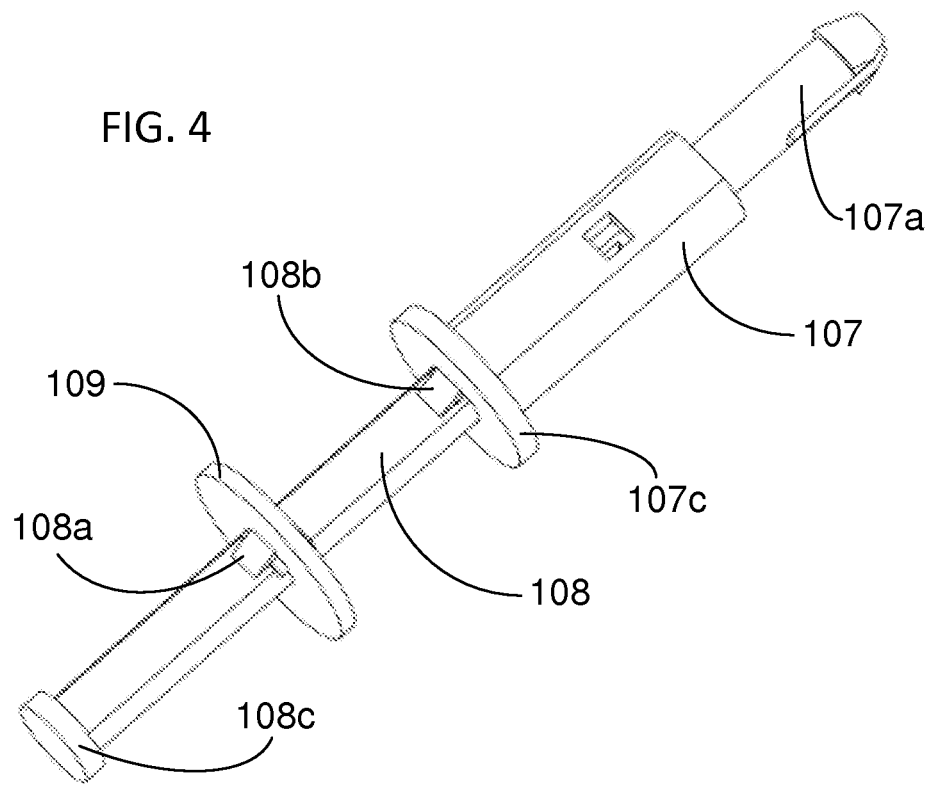
Figure 5:
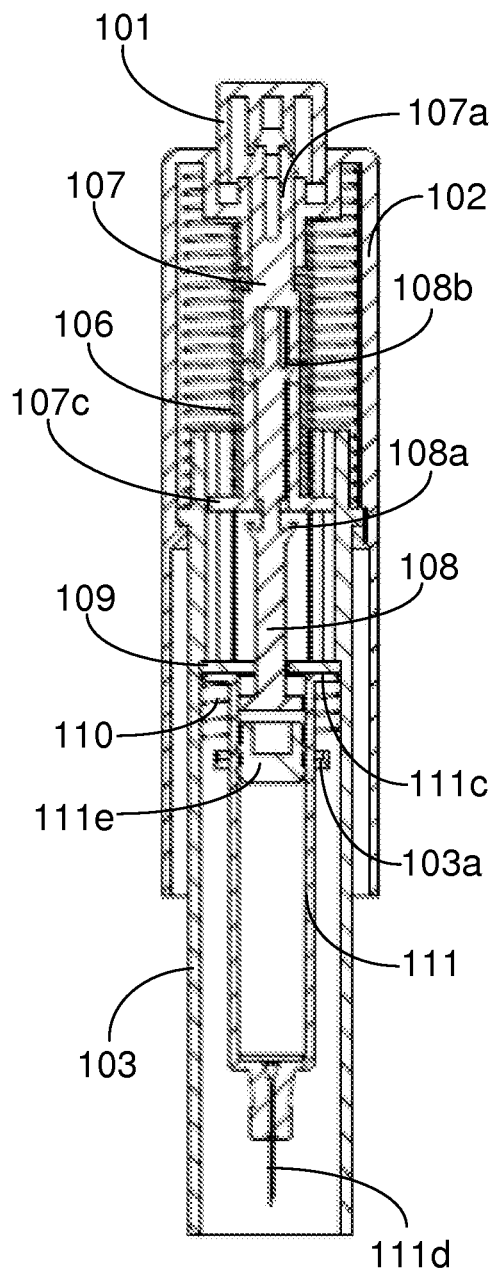
FIGS. 5 and 6 show operations of the first injection of the exemplary automatic medication injection device assembly according to the invention.
Figure 6:
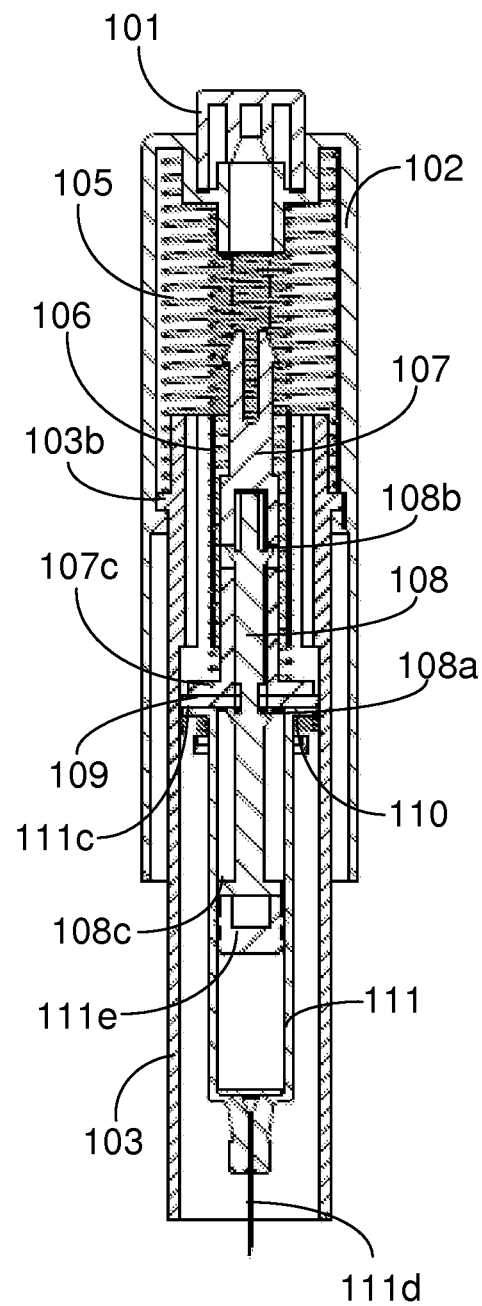
Figure 7:
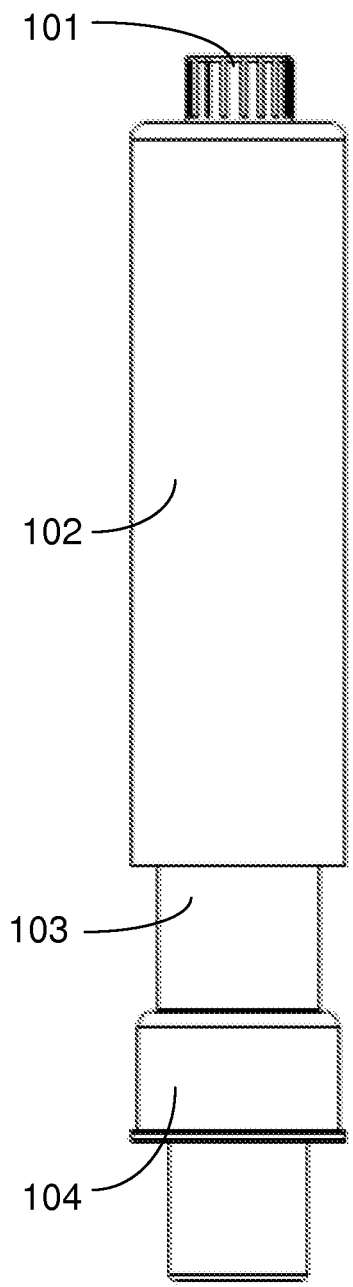
FIGS. 7 and 8 show re-arming operation, after the first injection, of the exemplary automatic medication injection device assembly according to the invention.
Figure 8:
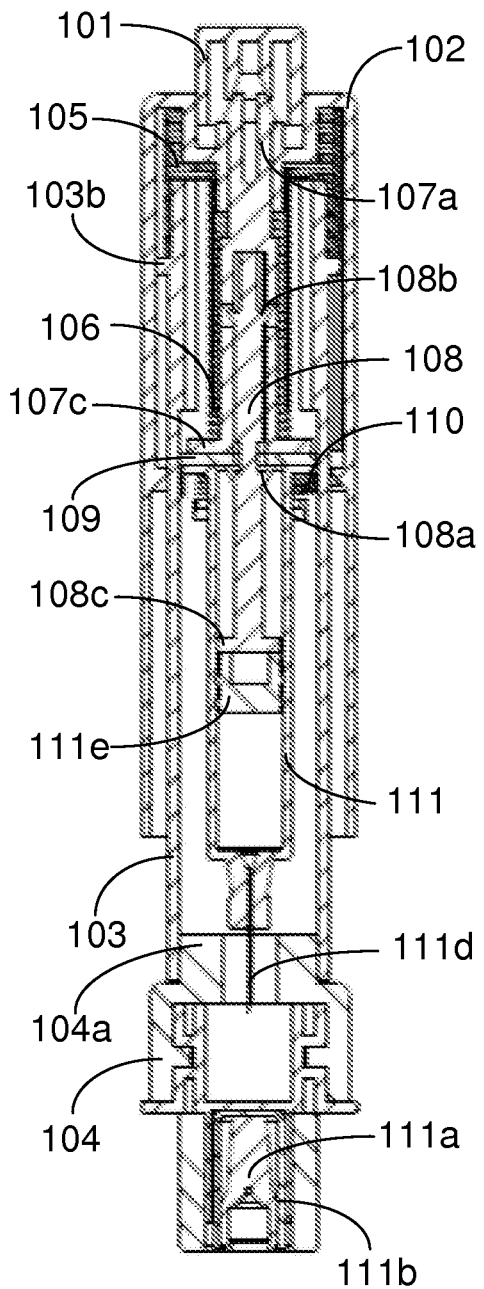
Figure 9:
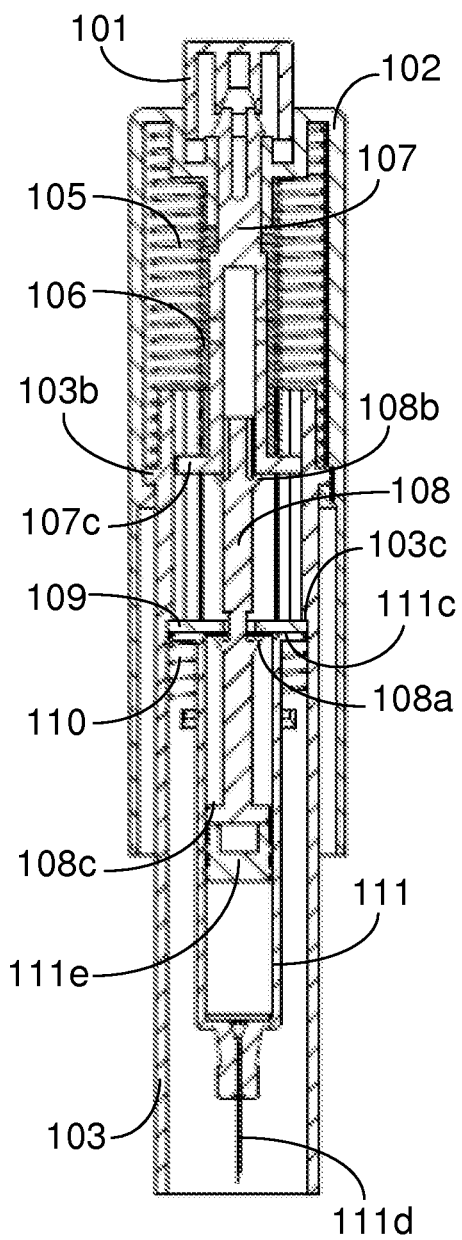
FIGS. 9 and 10 show operations of the second injection of the exemplary automatic medication injection device assembly according to the invention.
Figure 10:
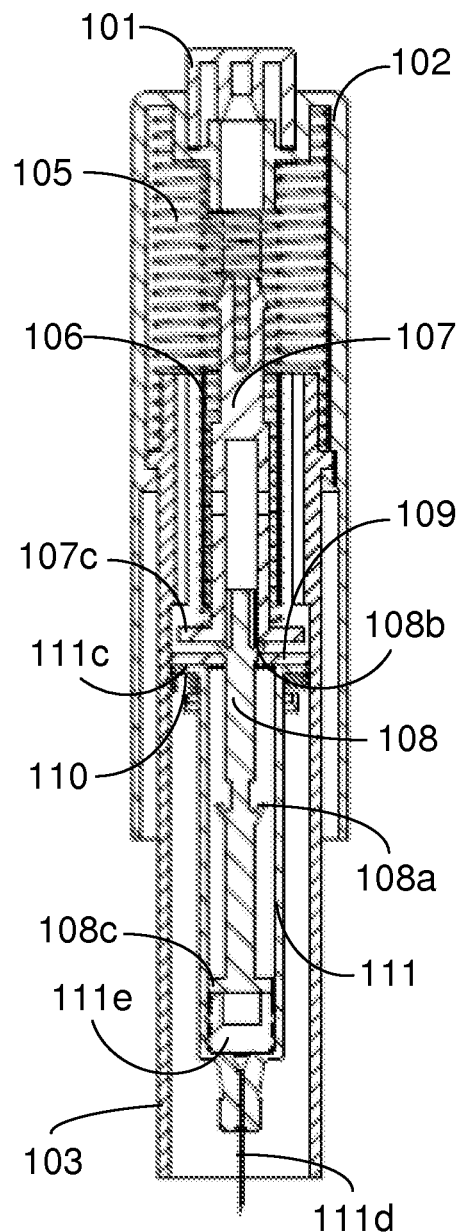

The present invention will become more fully understood from the detailed description given hereinbelow and the accompanying drawings which are given by way of illustration only, and thus, are not limitive of the present invention, and wherein:

The apparatus and methods presented herein can be used for delivering any of a variety suitable therapeutic agents or substances, such as a drug, into a patient. Initially it may be convenient to define that, the term "distal end" is meant to refer to the end of the automatic medication injection device assembly inserted into the patient, whereas the term "proximal end" is meant to refer to the end opposite to the "distal end" along the longitudinal axis of the device body. The words "upward", "downward", "upper", "lower", "right" and "left" designate directions in the drawings to which reference is made. The words "inward" and "outward" refer to directions toward and away from, respectively, FIGS. 1-12 illustrate the construction and function mechanism of an exemplary automatic medication injection device assembly 10 according to the invention. In this exemplary automatic medication injection device assembly 10, a pre-filled syringe 111 is used as medication container. A push cap 101, placed at the proximal end of the device assembly 10, is used to activate an automatic injection. The push cap 101 is assembled together with an upper cylinder 102. The upper cylinder 102 is further assembled with a lower cylinder 103. There is a separation spring 105 between the upper cylinder 102 and the lower cylinder 103 and landed on a landing feature 103b on the lower cylinder 103. There is an end unit 104 placed at the distal end of the device assembly 10. Inside the device assembly 10, there is a push rod assembly. With reference to FIGS. 3 and 4, the push rod assembly includes a push rod sheath 107, a push rod 108 and a stopping disk 109. On the push rod 108, there are two pairs of one-way bendable arms 108a and 108b. At the distal end of the push rod 108, there is a push disk feature 108c. At the proximal end of the push rod sheath 107, there are two fingers which are provided with outwardly projecting retaining barbs indicated by 107a. At the distal end of the push rod sheath 107, there is a landing feature 107c. A compressed driving spring 106 is placed between the landing feature 107c and the upper cylinder 102. Opening feature 107b is provided on the push rod sheath 107 for resting the one-way bendable arms 108b. With reference to FIG. 5, before use, the end unit 104 together with needle shield 111a and needle shield outer 111b on the pre-filled syringe 111 are removed. With reference to FIG. 6, during the first injection, the push cap 101 is pushed distally. The push cap 101 is provided with preferably an annular projection, which is arranged to squeeze the retaining barbs 107a at the proximal end of push rod sheath 107 so that the feature 107a have cleared from the upper cylinder 102. The push rod sheath 107 is thus released. The driving spring 106 applies force on feature 107c on the push rod 107 and pushes the push rod sheath 107 together with push rod 108 downward. The downward movement of the push rod 108, through the push disk feature 108c on the push rod 108, causes the downward movement of a movable piston 111e and the pre-filled syringe 111, due to hydraulic resistance. The first injection operation is enabled. Meantime, a syringe supporting spring 110, located between the flange feature 111c on the pre-filled syringe 111 and a landing feature 103a on the lower cylinder 103, is compressed. The downward movement of the pre-filled syringe 111 stops when the syringe supporting spring 110 is fully compressed. Or, the downward movement of the pre-filled syringe may be stopped by when the flange feature 111c meets with a stopping feature on the lower cylinder 103. When the push rod 108 moves downward, the first pair of one-way bendable arms 108a pass through the stopping disk 109. FIGS. 7-9 show the re-setting or re-arming of the device assembly 10. Before the re-arming operation, the end unit 104 is re-assembled with the device assembly 10 in a reversed direction in order to utilize the opening portion 104a on the end unit 104 to cover the needle 111d on the pre-filled syringe 111. During the re-arming operation, the upper cylinder 102 is pushed distally and the separation spring 105 is compressed, so that the upper cylinder 102 is re-engaged with the retaining bars 107a on the push rod sheath 107. When the distal pushing force on the upper cylinder 102 is removed, the separation spring 105 pushes the upper cylinder 102 upward. Because of the retaining bars 107a, the push rod sheath 107 also moves upward accordingly. In absence of downward pushing force, the syringe support syringe 110 moves the pre-filled syringe 111, through flange feature 111c, and the stopping disk 109 to an upper position. The upward movement of the stopping disk 109 stops at a blocking feature 103c on the lower cylinder 103. Because of the stopping disk 109 and the one-way bendable arms 108a, the upward movement of the push rod 108 is also stopped. Consequently, the push rod 108 is pulled and extended out from the push rod sheath 107 and the second pair of the one-way bendable arm 108b pass out of the push rod sheath 107. With reference to FIG. 10, during the second injection, the push cap 101 is pushed distally and the retaining bars 107a have cleared from the upper cylinder 102, again. The push rod sheath 107 is thus released. The driving spring 106 applies force on the feature 107c on the push rod sheath 107 and pushes the push rod sheath 107 downward. This time, the downward movement of the feature 107c on the push rod sheath 107 applies pushing force on the second pair of the one-way bendable arm 108b on the push rod 108 to cause the push rod 108 move downward.

Figure 11:
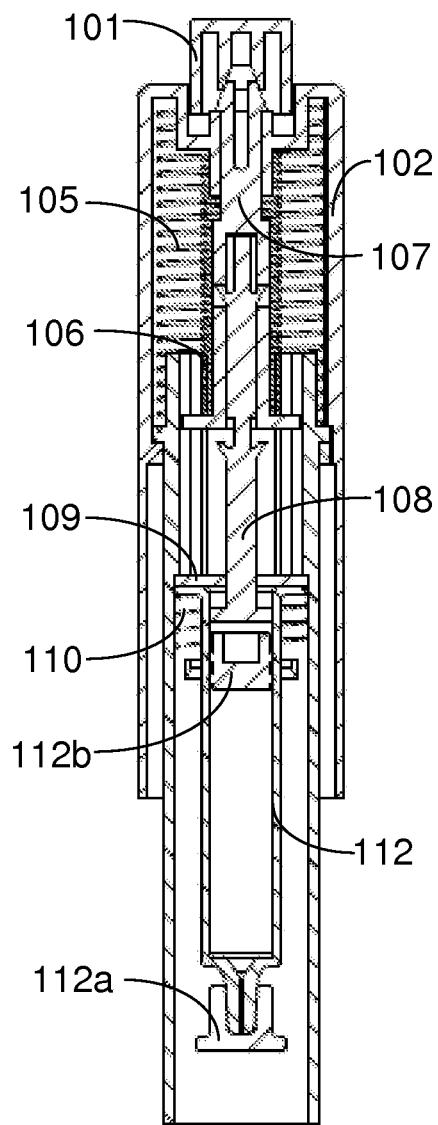
FIGS. 11 and 12 show the exemplary automatic medication injection device assembly according to the invention, with another medication container.
Figure 12:
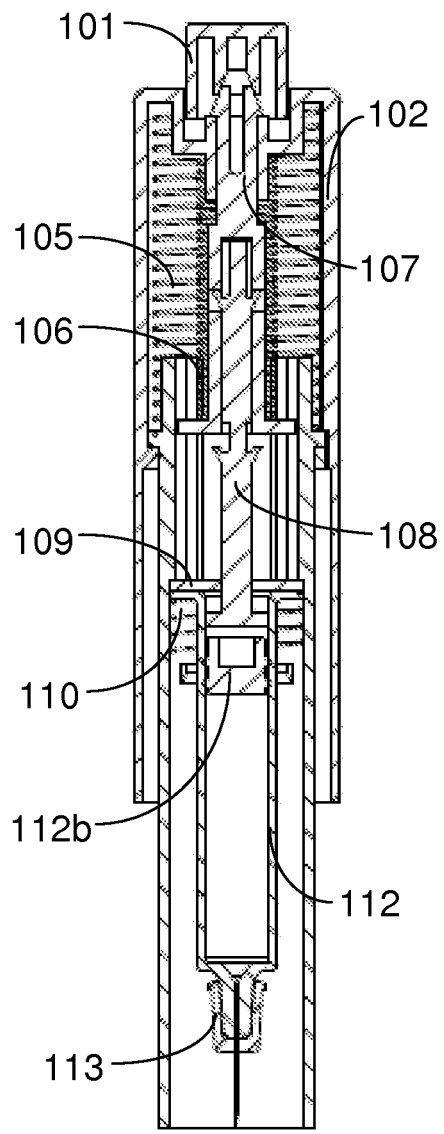
Figure 13:
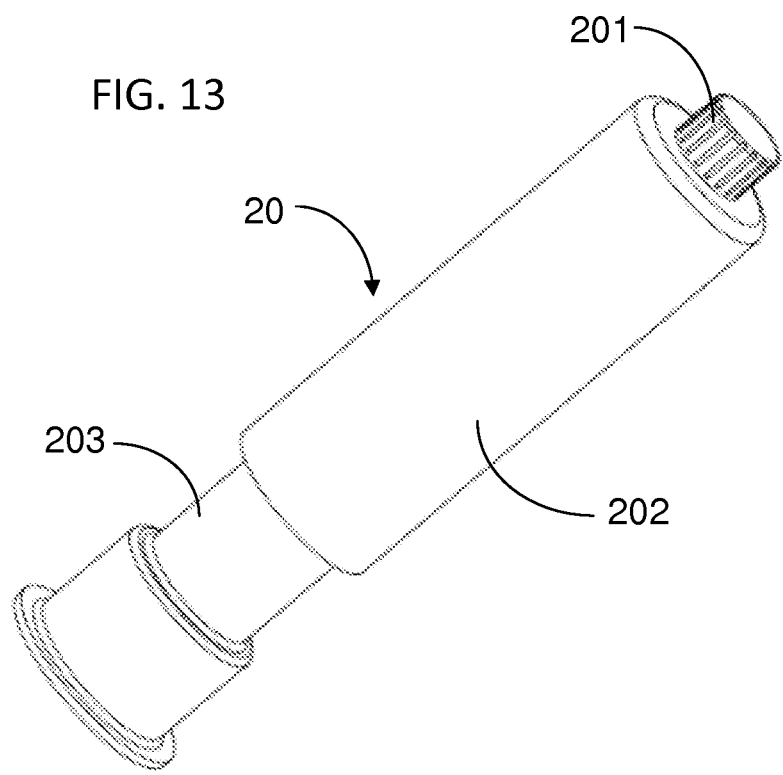
FIG. 13 is a perspective view of the first alternative automatic medication injection device assembly according to the invention.
Figure 14:
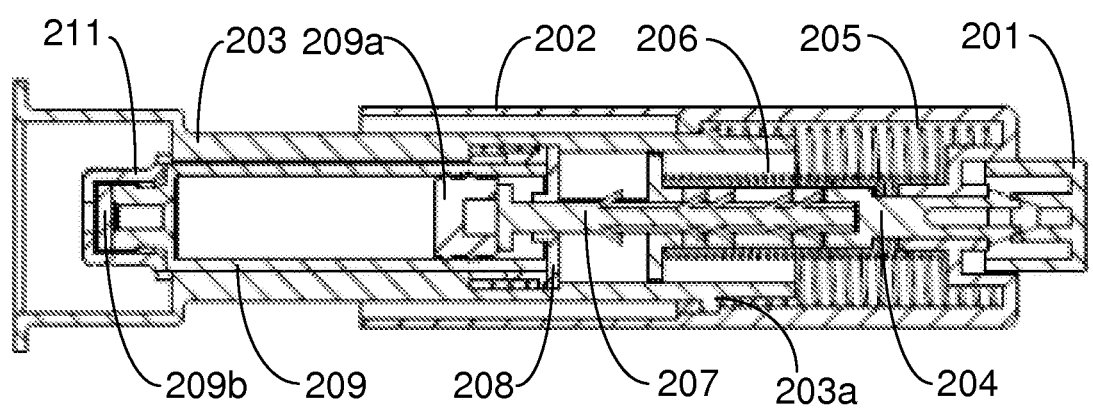
FIG. 14 shows a cross-sectional view of the first alternative automatic medication injection device assembly according to the invention.

The downward movement of the push rod 108, through the push disk feature 108c on the push rod 108, causes the further downward movement of a movable piston 111e and downward movement of the pre-filled syringe 111, due to hydraulic resistance. The second injection operation is enabled. With the same operation mechanism, more than two pairs of one-way bendable arms can be placed on the push rod 18 in order to conduct more than two sequential injections by using the device assembly 10. FIGS. 11 and 12 show another configuration of the exemplary automatic medication injection device assembly 10. In this configuration, instead of using the pre-filled syringe 111 with a staked needle, a pre-filled syringe 112 with luer lock connection is used. Before injection, the pre-filled syringe 112 is sealed by a luer lock tip cap 112a and a movable piston 112b. During injection, the luer lock tip cap 112a is removed and a luer lock needle 113 is assembled together with the pre-filled syringe 112.

Figure 15:
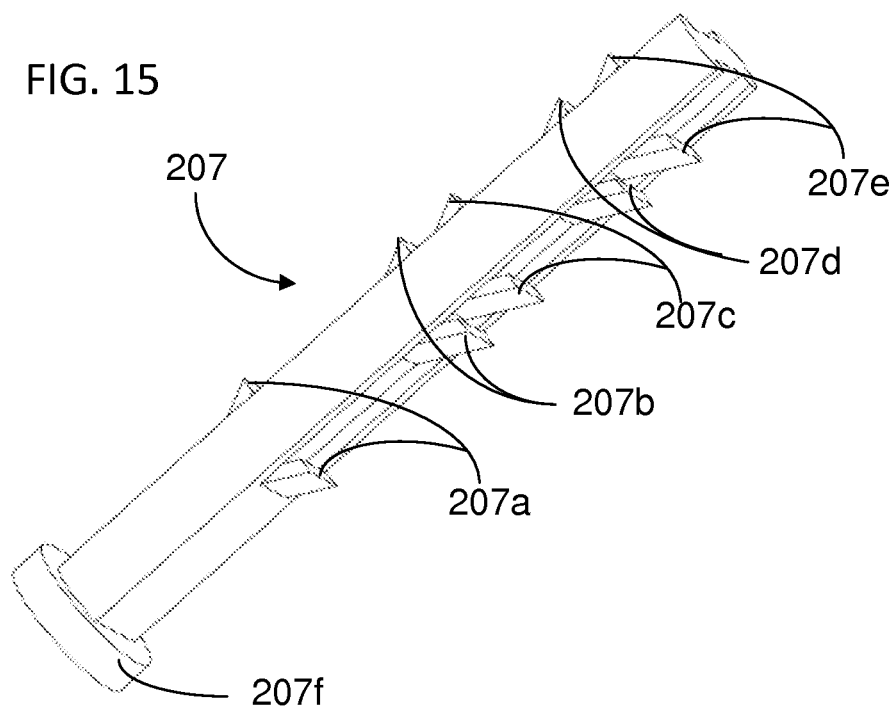
FIGS. 15 and 16 show a push rod assembly of the first alternative automatic medication injection device assembly according to the invention.
Figure 16:
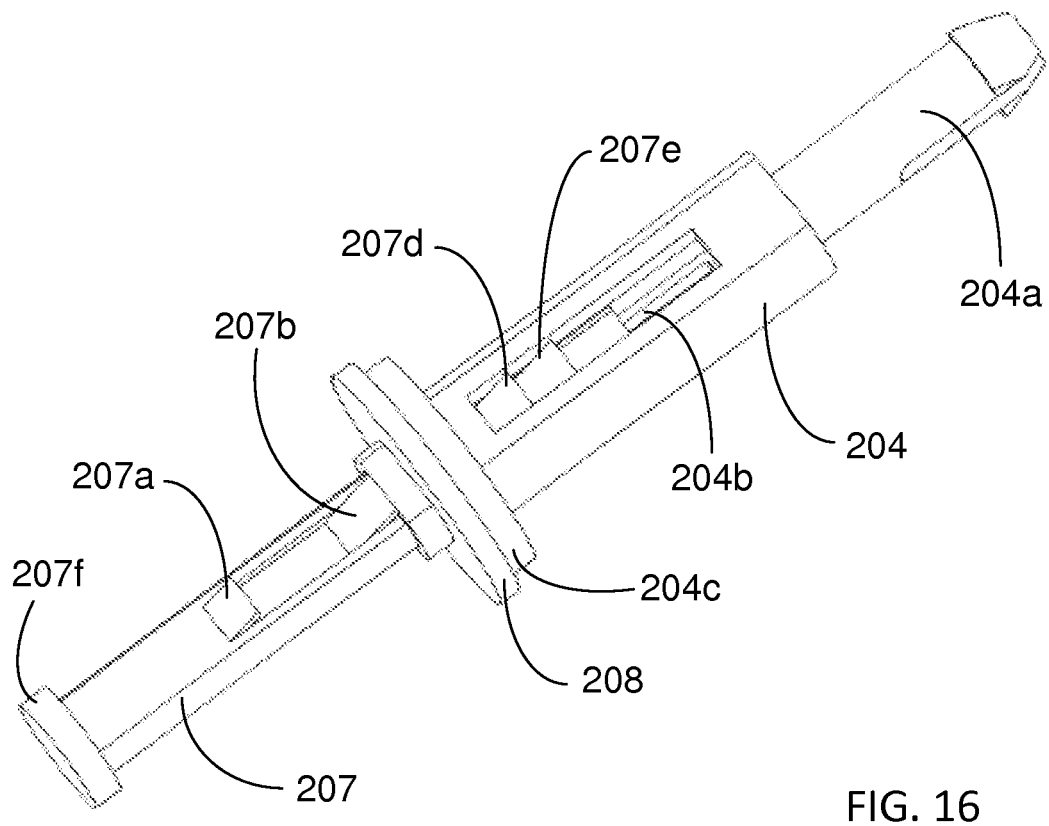
Figure 17:
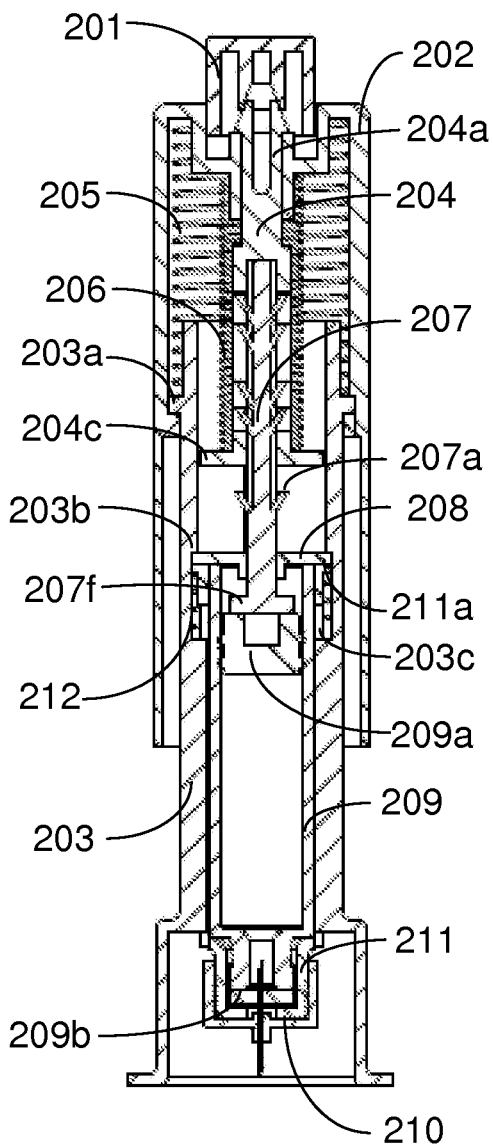

FIGS. 13-24 illustrate the construction and function mechanism of the first alternative automatic medication injection device assembly 20 according to the invention. In this exemplary automatic medication injection device assembly 20, a pre-filled cartridge 209 is used as medication container. A push cap 201, placed at the proximal end of the device assembly 20, is used to activate an automatic injection. The push cap 201 is assembled together with an upper cylinder 202. The upper cylinder 202 is further assembled with a lower cylinder 203. There is a separation spring 205 between the upper cylinder 202 and the lower cylinder 203 and landed on a landing feature 203a on the lower cylinder 203. Inside the device assembly 20, there is a push rod assembly. With reference to FIGS. 15 and 16, the push rod assembly includes a push rod sheath 204, a push rod 207 and a stopping disk 208. On the push rod 207, there are five pairs of one-way bendable arms, 207a, 207b, 207c, 207d and 207e. At the distal end of the push rod 207, there is a push disk feature 207f. At the proximal end of the push rod sheath 204, there are two fingers which are provided with outwardly projecting retaining barbs indicated by 204a. Opening feature 204b is provided on the push rod sheath 204 for resting the one-way bendable arms. At the distal end of the push rod sheath 204, there is a landing feature 204c. A compressed driving spring 206 is placed between the landing feature 204c and the upper cylinder 202. With reference to FIG. 17, before use, a double ended needle 210, for example, insulin pen needle, is assembled with a cartridge sheath 211, and the double ended needle 210 penetrates the septum 209b on the pre-filled cartridge 209.

Figure 18:
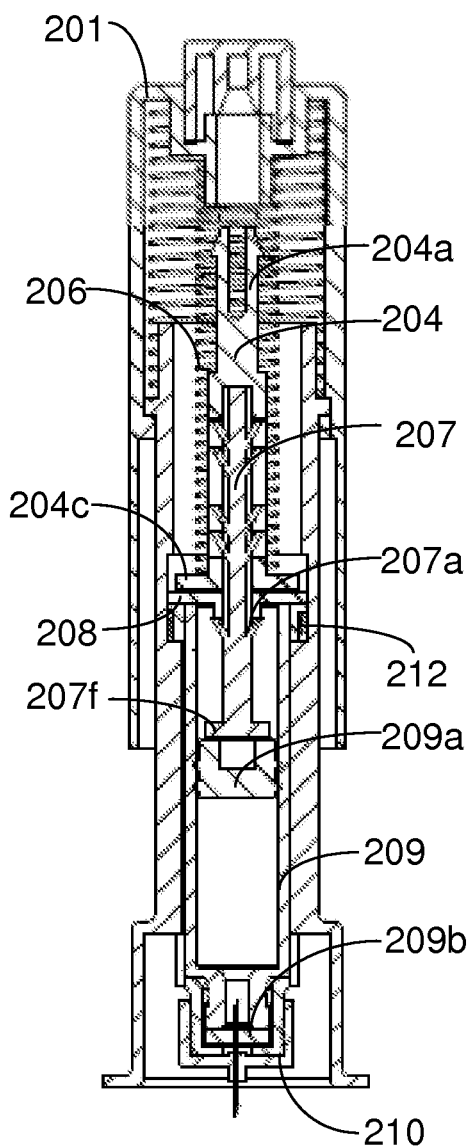
Figure 19:
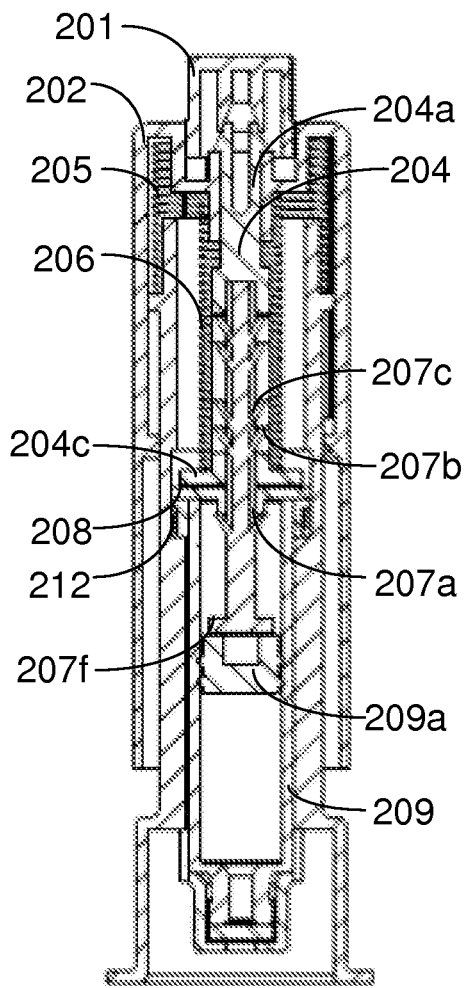
Figure 20:
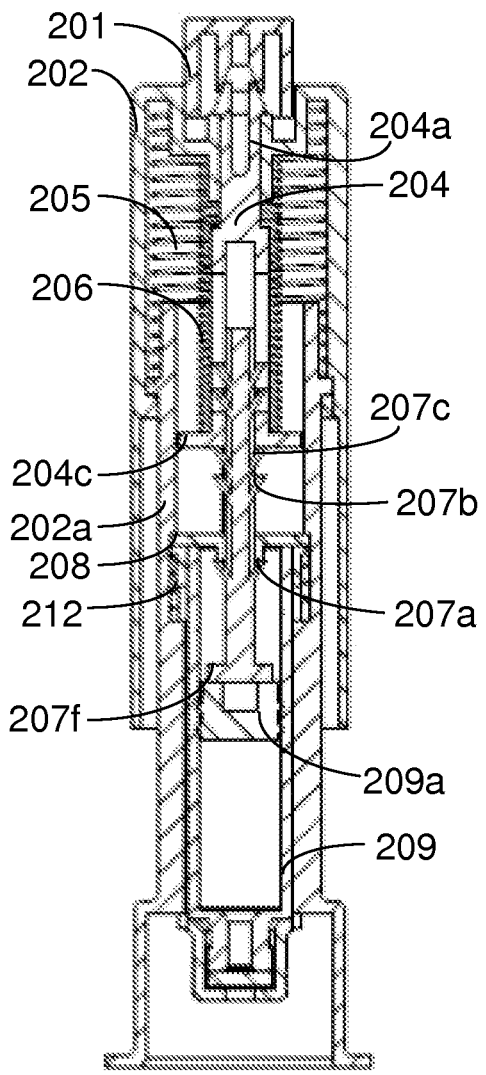
Figure 23:
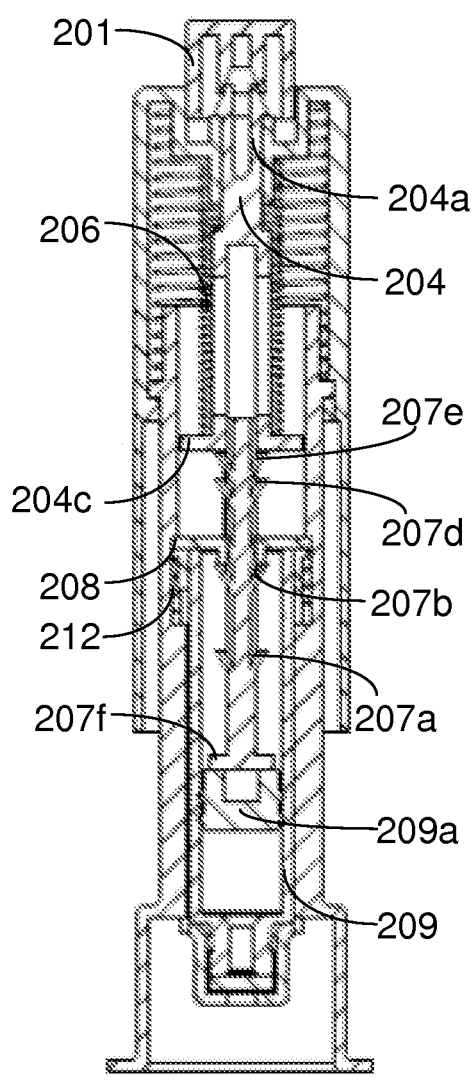
Figure 24:
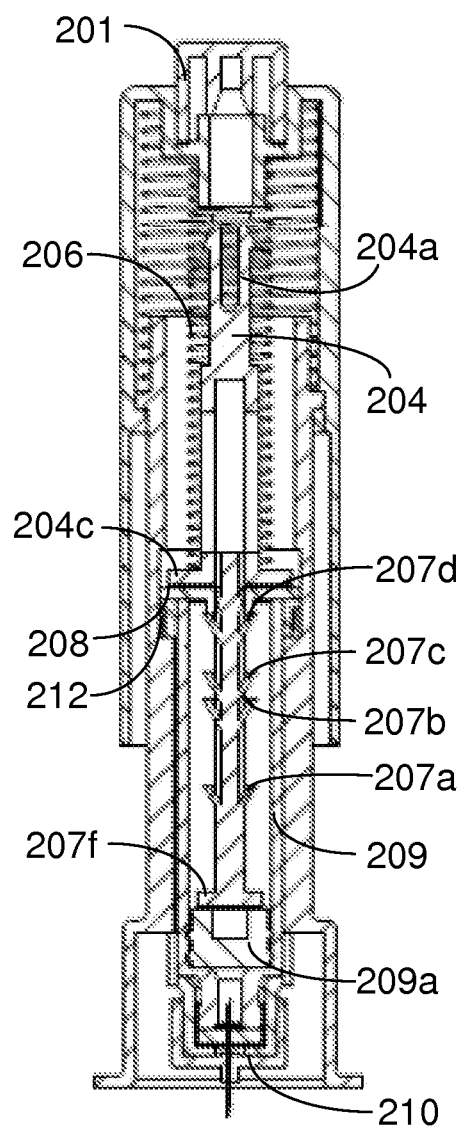
Figure 25:
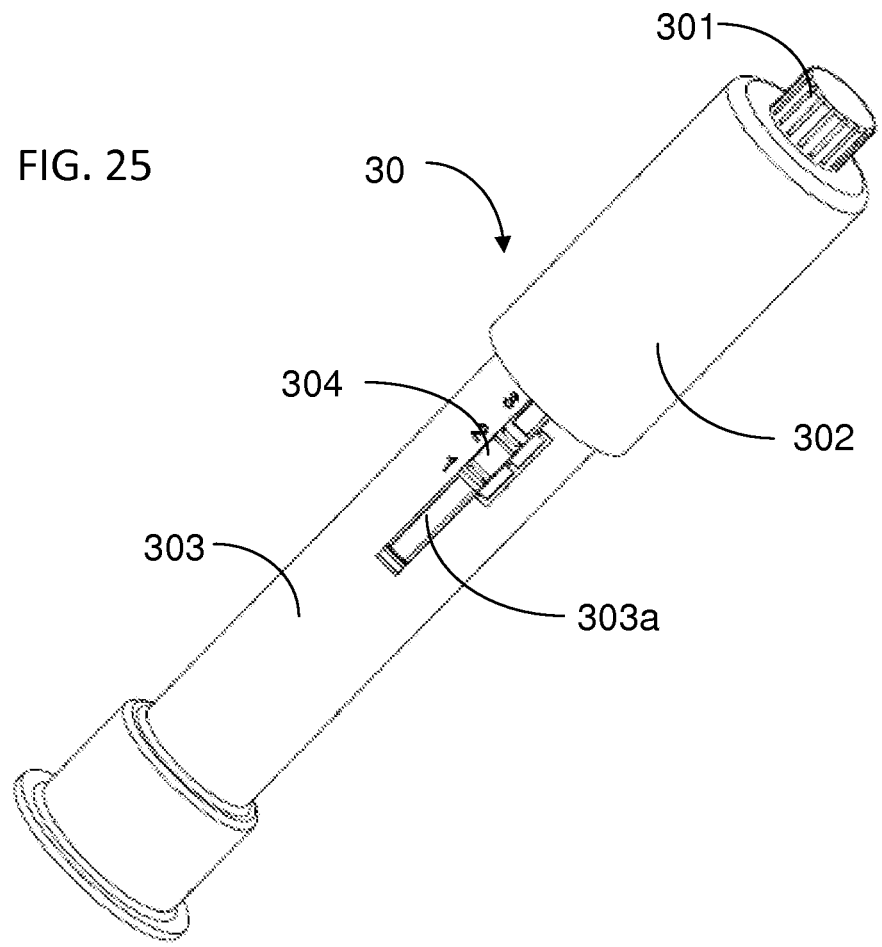
FIG. 25 is a perspective view of the second alternative automatic medication injection device assembly according to the invention.
Figure 26:
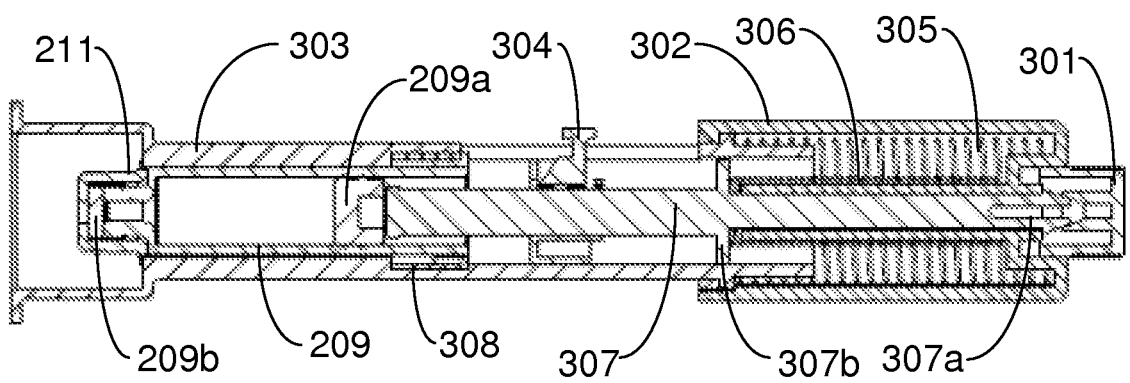
FIG. 26 shows a cross-sectional view of the second alternative automatic medication injection device assembly according to the invention.

With reference to FIG. 18, during the first injection, the push cap 201 is pushed distally. The push cap 201 is provided with preferably an annular projection, which is arranged to squeeze the retaining barbs 204a at the proximal end of push rod sheath 204 so that feature 204a have cleared from the upper cylinder 202. The push rod sheath 204 is thus released. The driving spring 206 applies force on the landing feature 204c on the push rod sheath 204 and pushes the push rod sheath 204 and push rod 207 downward. The downward movement of the push rod 207, through the push disk feature 207f on the push rod 207, causes the downward movement of a movable piston 209a and the cartridge sheath 211 and the pre-filled cartridge 209 and the double ended needle 210, due to hydraulic resistance. The first injection operation is enabled. Meantime, a cartridge supporting spring 212, located between the flange feature 211a on the cartridge sheath 211 and a landing feature 203c on the lower cylinder 203, is compressed, and the first pair of one-way bendable arms 207a pass through the stopping disk 208. FIGS. 19 and 20 show the re-setting or re-arming of the device assembly 10. Before the re-arming operation, the double ended needle 210 is removed. During the re-arming operation, the upper cylinder 202 is pushed distally and the separation spring 205 is compressed, so that the upper cylinder 202 is re-engaged with the retaining bars 204a on the push rod sheath 204. When the distal pushing force on the upper cylinder 202 is removed, the separation spring 205 pushes the upper cylinder 202 upward. Because of the retaining bars 204a, the push rod sheath 204 also moves upward accordingly. In absence of downward pushing force, the cartridge support spring 212 moves the cartridge sheath 211 and the pre-filled cartridge 209 and the stopping disk 208, through flange feature 211a, to an upper position. The upward movement of the stopping disk 208 stops at a blocking feature 203b on the lower cylinder 203. Because of the stopping disk 208 and the one-way bendable arms 207a, the upward movement of the push rod 207 is also stopped. Consequently, the push rod 207 is pulled and extended out from the push rod sheath 204 and the second and third pairs of the one-way bendable arm 207b and 207c passes out of the push rod sheath 204. Before the second injection, a new double ended needle 210 is assembled with the device assembly 20. With reference to FIG. 21, during the second injection, the push cap 201 is pushed distally and the retaining bars 204a have cleared from the upper cylinder 202, again. The push rod sheath 204 is thus released. The driving spring 206 applies force on the landing feature 204c on the push rod 204 and pushes the push rod sheath 204 downward. This time, the downward movement of the landing feature 204c applies pushing force on the third pair of the one-way bendable arm 207c on the push rod 207 to cause the push rod 207 move downward. The downward movement of the push rod 207, through the push disk feature 207f on the push rod 207, causes the further downward movement of the movable piston 209a and downward movement of the pre-filled cartridge 209 and the cartridge sheath 211 and the double ended needle 210. The second injection operation is enabled. Meantime, the second pair of one-way bendable arms 207b pass through the stopping disk 208 and will provide the function of arms 207a, for the next step operation. FIG. 23 shows the device assembly 20 before the third injection and FIG. 24 shows the device assembly 20 during the third injection. For the third injection, the downward push force from the push rod sheath 204 is applied on the fifth pair of the one-way bendable arm 207e.

Figure 27:
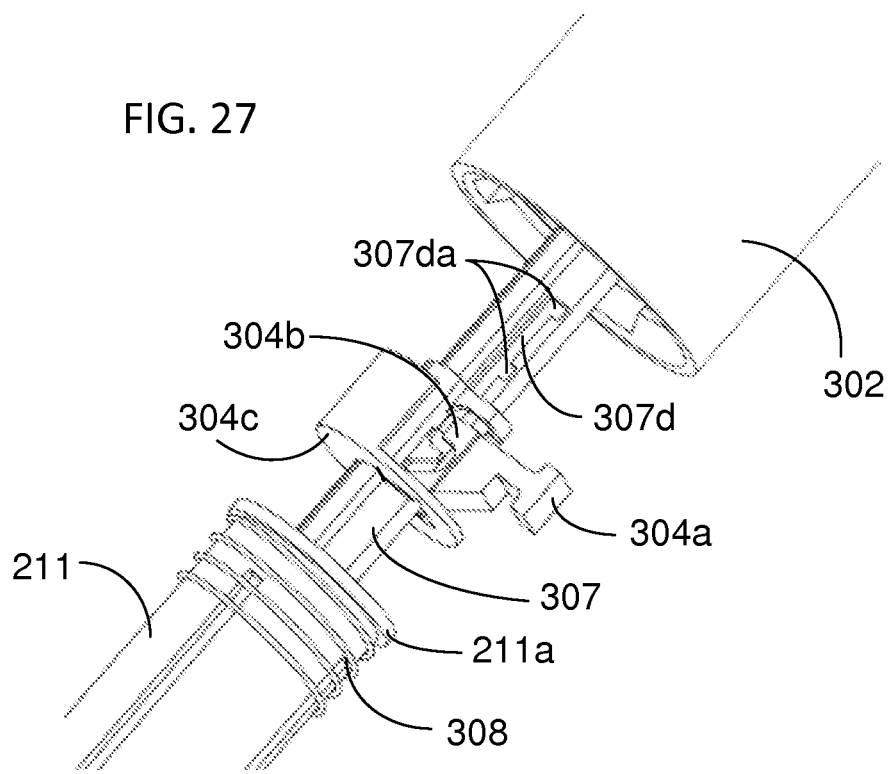
FIGS. 27 and 28 show the position setting mechanism for multiple dosing using the second alternative automatic medication injection device assembly according to the invention.
Figure 28:
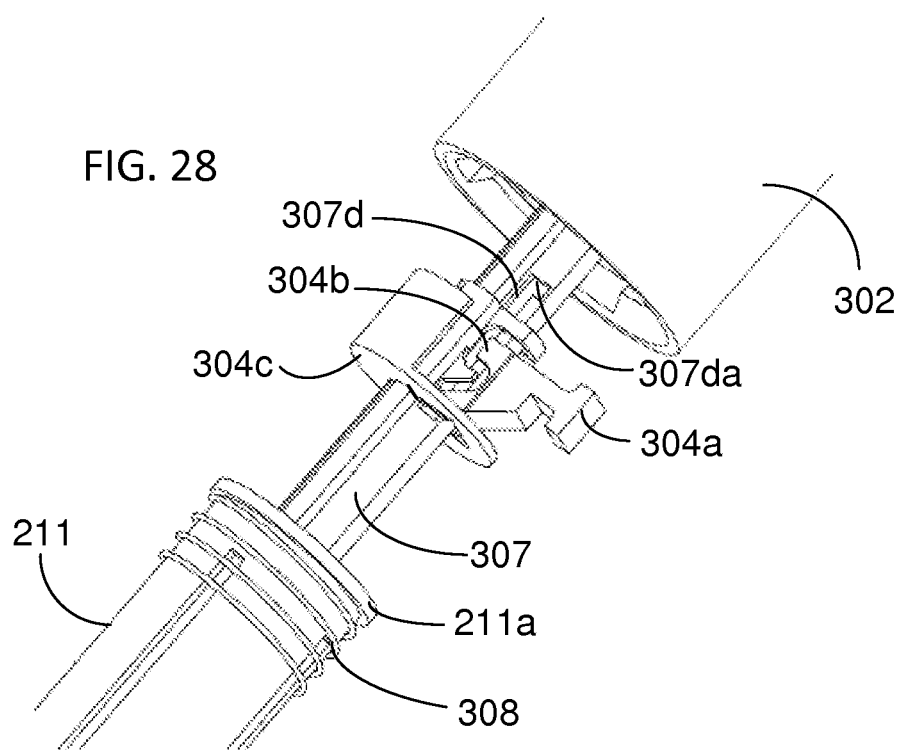

FIGS. 25-32 illustrate the construction and function mechanism of the second alternative automatic medication injection device assembly 30 according to the invention. In this exemplary automatic medication injection device assembly 30, the pre-filled cartridge 209 is used as medication container. A push cap 301, placed at the proximal end of the device assembly 30, is used to activate an automatic injection. The push cap 301 is assembled together with an upper cylinder 302. The upper cylinder 302 is further assembled with a lower cylinder 303. A dose setting window 303a being defined on the lower cylinder 303. There is a separation spring 305 between the upper cylinder 302 and the lower cylinder 303. Inside the device assembly 30, there is a push rod assembly. With reference to FIGS. 27 and 28, the push rod assembly includes a position blocker 304 and a push rod 307. On the push rod 307, there is positioning track feature 307d. In the positioning track feature 307d, there are a plurality of indexed spaced-apart position setting features 307da. A protrusion feature 304b on the position blocker 304 is locked in the different individual position setting feature 307da for multiple injections. In order to move the position blocker 304 to different position along the push rod 307, user pushes the push a tab feature 304a on the position blocker 304 inward (toward to the center of the device assembly 30). Then, the protrusion feature 304b is dislocated out from the position setting feature 307da and the position blocker 304 can be moved along the longitudinal axis of the push rod 307.

Figure 29:
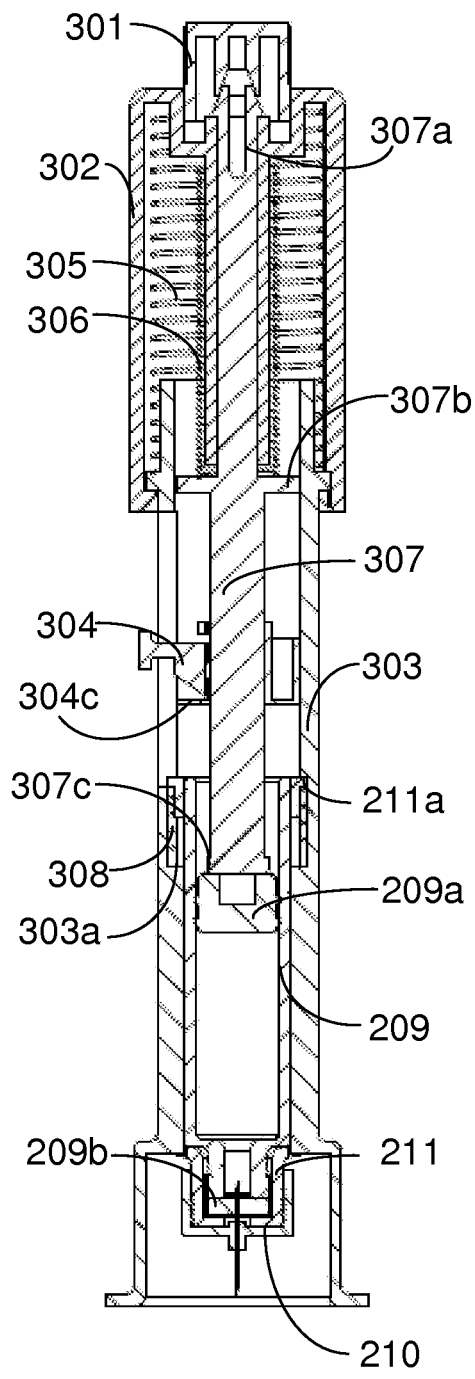
FIGS. 29 and 30 show operations of an injection of the second alternative automatic medication injection device assembly according to the invention.
Figure 30:
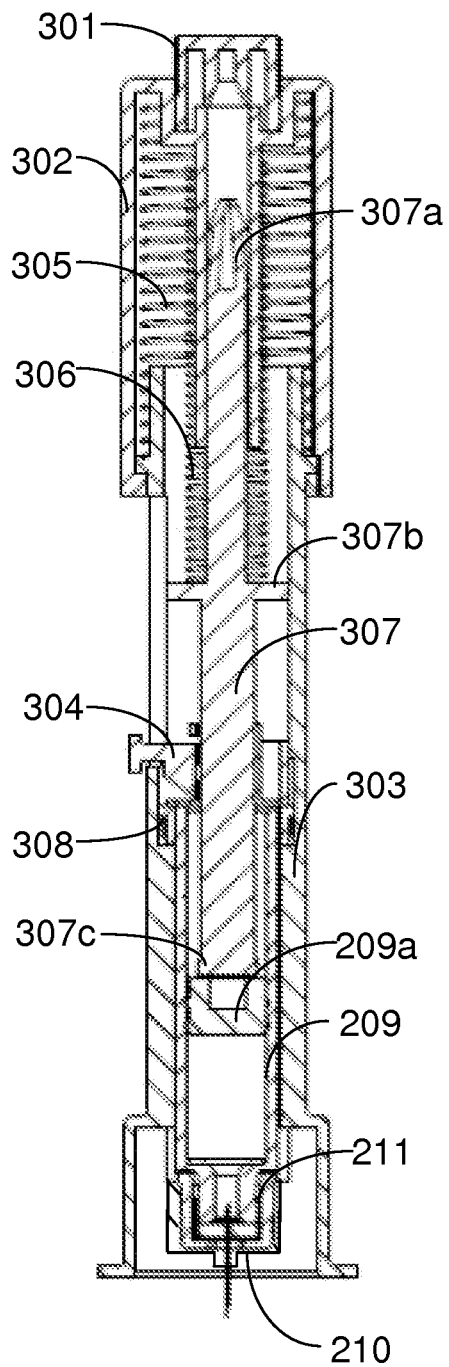
Figure 31:
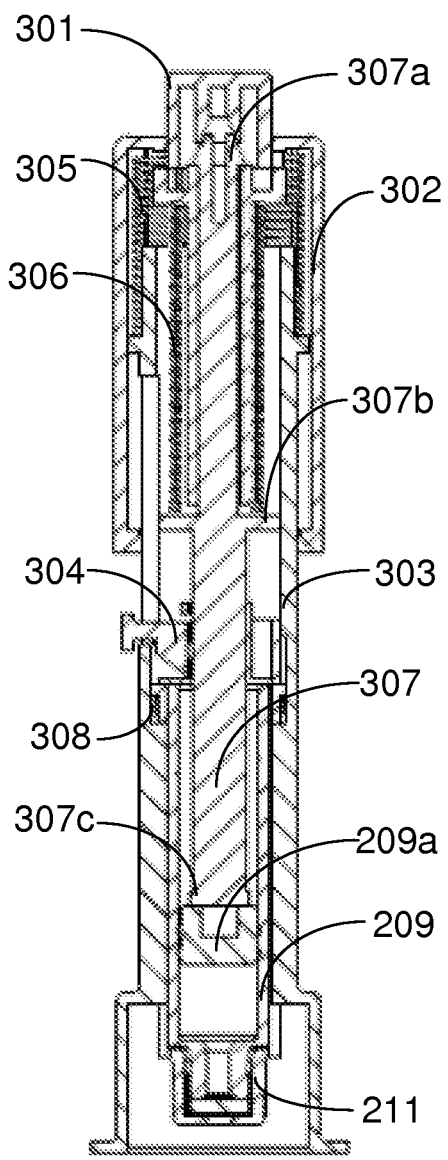
FIGS. 31 and 32 show a re-arming operation of the second alternative automatic medication injection device assembly according to the invention.
Figure 32:
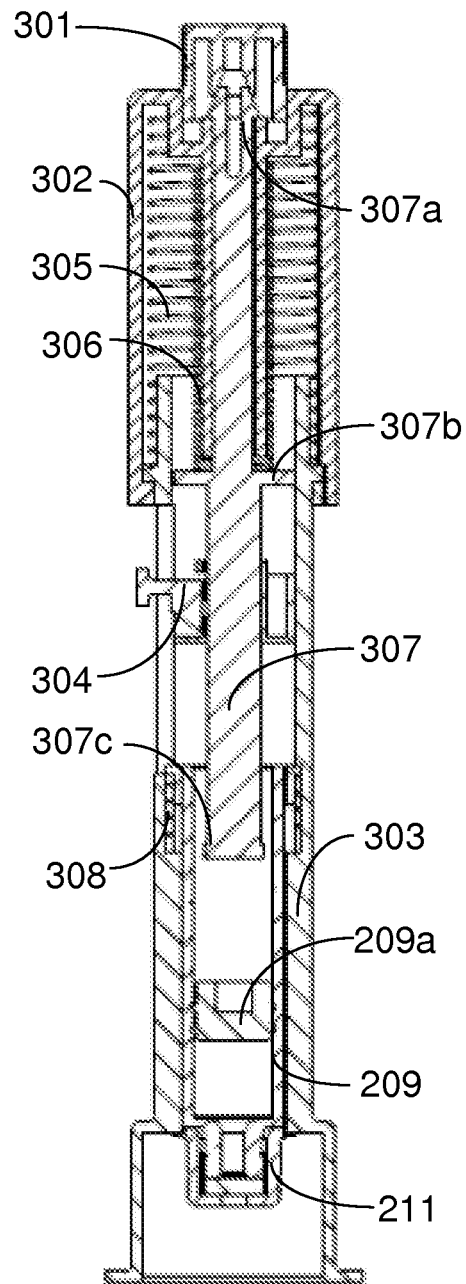

When the position blocker 304 is moved to the next position, the push tab feature 304a is released and the protrusion feature 304b is locked in a different position setting feature 307da. FIGS. 27 and 28 show the position blocker 304 is at different locations. At the distal end of the position blocker 304, there is a push disk feature 304c. A compressed driving spring 306 is placed between a landing feature 307b on the push rod 307 and the upper cylinder 302. With reference to FIGS. 29 and 30, during an injection, the push cap 301 is pushed distally. The push cap 301 is provided with preferably an annular projection, which is arranged to squeeze the retaining barbs 307a at the proximal end of push rod 307 so that retaining barbs 307a have cleared from the upper cylinder 302. The push rod 307 is thus released. The driving spring 306 applies force on the landing feature 307b on the push rod 307 and pushes the push rod 307 together with the position blocker 304 downward. The downward movement of the push rod 307, through an end feature 307c, causes the downward movement of the movable piston 209a and the cartridge sheath 211 and the pre-filled cartridge 209 and the double ended needle 210 due to hydraulic resistance. Thus, an injection operation is enabled. Meantime, a cartridge supporting spring 308, located between the flange feature 211a on the cartridge sheath 211 and a landing feature 303a on the lower cylinder 303, is compressed. The downward movement of the position blocker 304 stops when the cartridge supporting spring 308 is fully compressed, and one of multiple injections is completed. FIGS. 31 and 32 show the re-setting or re-arming of the device assembly 30. Before the re-arming operation, the double ended needle 210 is removed. During the re-arming operation, the upper cylinder 302 is pushed distally and the separation spring 305 is compressed, so that the upper cylinder 302 is re-engaged with the retaining bars 307a on the push rod 307. When the distal pushing force on the upper cylinder 302 is removed, the separation spring 305 pushes the upper cylinder 302 upward. Because of the retaining bars 307a, the push rod 307 also moves upward accordingly. In absence of downward pushing force, the cartridge support spring 308 moves the cartridge sheath 211 and the pre-filled cartridge 209, through flange feature 211a, to an upper position. For the subsequential injection, user can move the position blocker 304 proximally in order to deliver more medication out of the pre-filled cartridge 209.

Figures 33, 34:
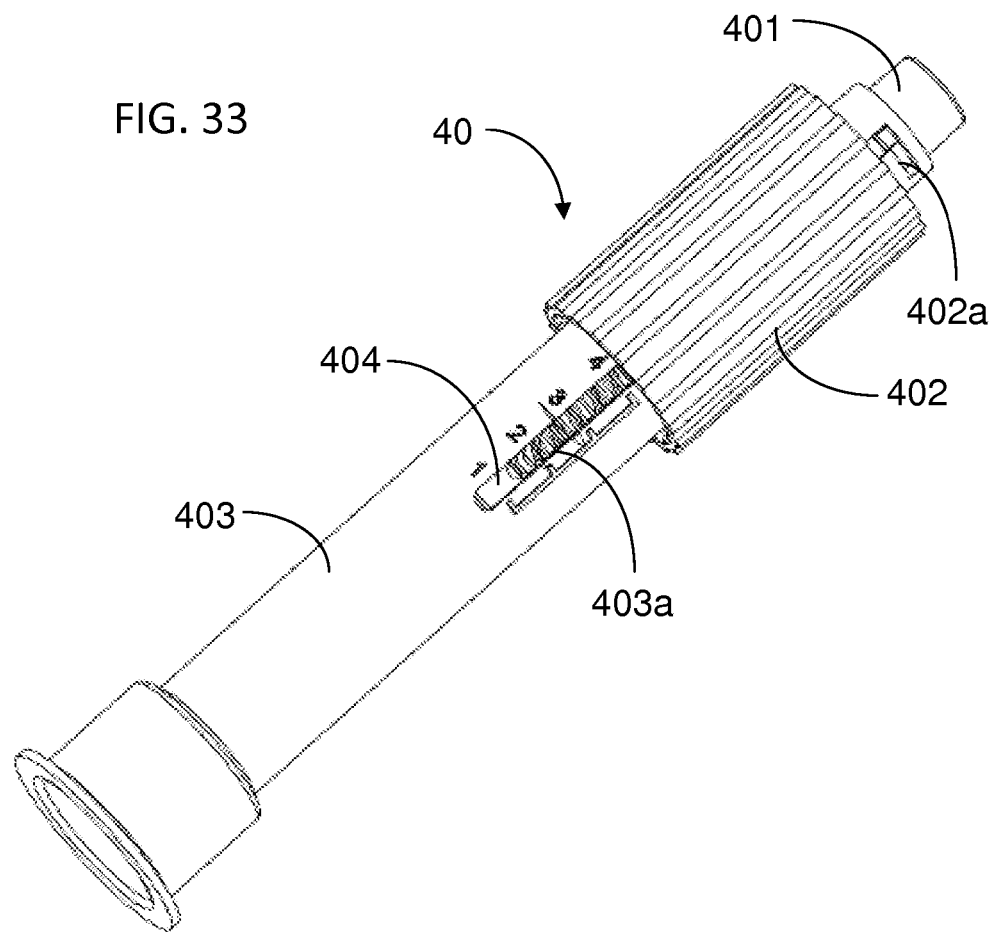
FIG. 33 is a perspective view of the third alternative automatic medication injection device assembly according to the invention.
FIG. 34 shows a cross-sectional view of the third alternative automatic medication injection device assembly according to the invention.
Figure 38:
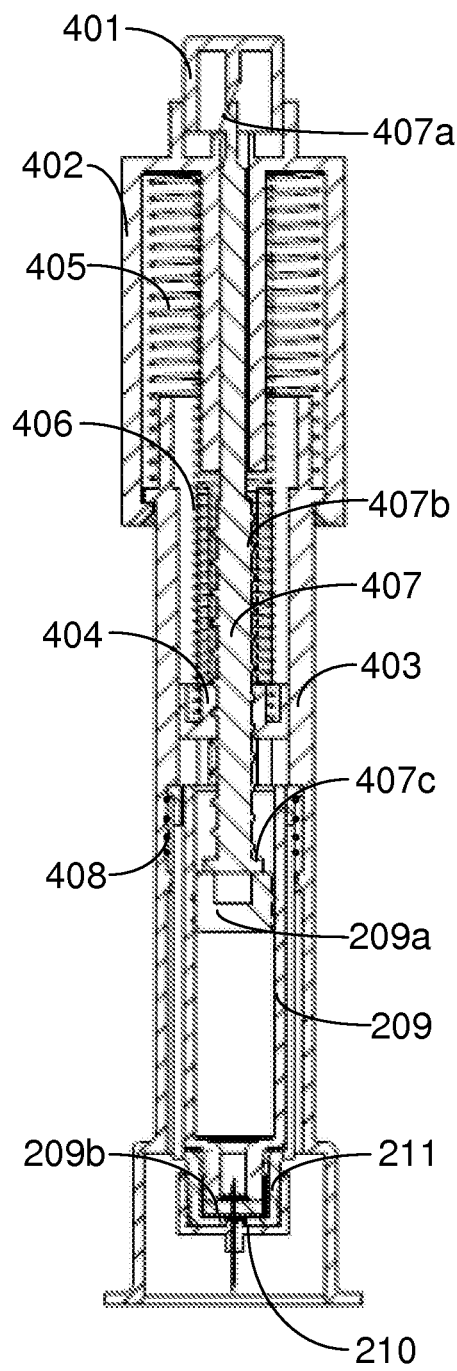
FIGS. 38 and 39 show the third alternative automatic medication injection device assembly, before the first and a latter injection, according to the invention.
Figure 39:
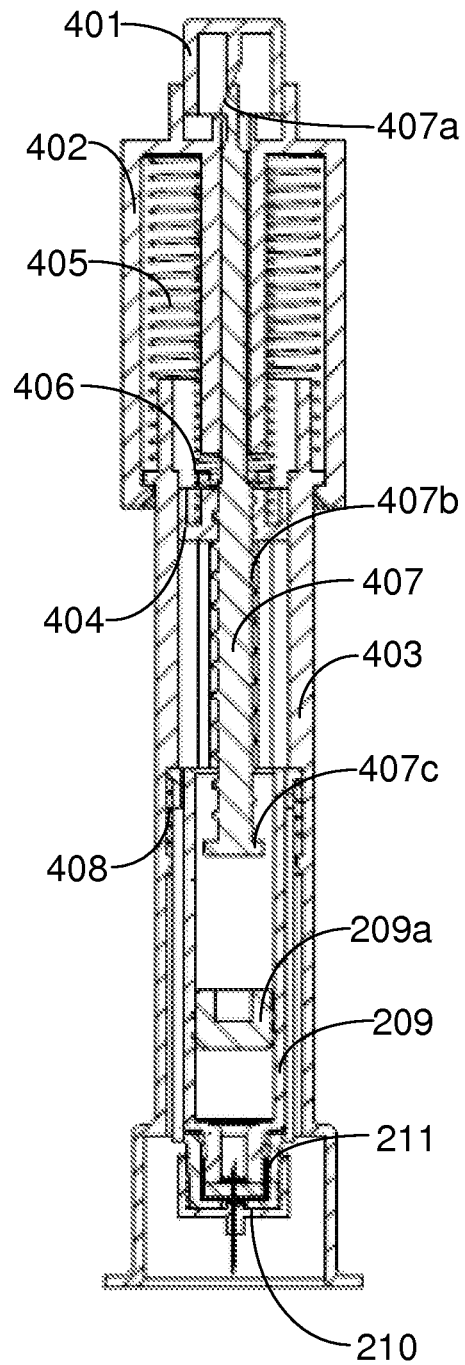

FIGS. 33-39 illustrate the construction and function mechanism of the third alternative automatic medication injection device assembly 40 according to the invention. In this exemplary automatic medication injection device assembly 40, the pre-filled cartridge 209 is used as medication container. A push cap 401 is assembled with a dialing cylinder 402, through a track 402a on the dialing cylinder 402. This engagement prevents accidental activation of the device before use. A dose setting window 403a being defined on a scale cylinder 403. During use, the dialing cylinder 402 is rotated to set the injection dose. With reference to FIG. 34, user sets the location of a stopping ring 404 in order to get the different injection doses. Meantime, before injection, the automatic medication injection device assembly 40 is shown with a push rod 407 in a locked state, against biasing force of a driving spring 406, by a releasable latch mechanism formed between a hook feature 407a on the push rod 407 and the dialing cylinder 402. The pre-filled cartridge 209 is assembled together with the scale cylinder 403 through the cartridge sheath 211. FIG. 35 shows the engagements between the push rod 407 and the dialing cylinder 402. A rectangular shape channel feature 402a on the dialing cylinder 402 engages with flat surfaces 407b on the push rod 407. When user rotates the dialing cylinder 402, the push rod 407 rotates accordingly. The rectangular shape channel feature 402a further provides landing surface for the releasable hook feature 407a on the push rod 407. FIG. 36 shows engagements among the push rod 407, the stopping ring 404 and the scale cylinder 403. During the dose setting, user rotates the dialing cylinder 402 and the push rod 407 relative to the scale cylinder 403. Because of a thread feature 407c on the push rod 407, when the push rod 407 rotates, the stopping ring 404 moves up and down along axial of the device, through the thread engagement between the push rod 407 and stopping ring 404. The location of the stopping ring 404 can be viewed through viewing window 403a on the scale cylinder 403. Due to the constrain engagement between groove feature 404a on the stopping ring 404 and rail feature 403b on the scale cylinder 403, the stopping ring 404 can only moves axially, but not radially along the push rod 407 during dose setting and during injection. FIG. 37 shows the engagement between the dialing cylinder 402 and the scale cylinder 403. In operation steps other than the dose setting step, the dialing cylinder 402 is always locked with the scale cylinder 403 together, through a tooth engagement between feature 402b on the dialing cylinder 402 and feature 403c on the scale cylinder 403, or some other mechanism which allows the components to be connected and disconnected from each other. This tooth-type lock engagement prevents free rotation of the dialing cylinder 402 and restrain the radial movement and back-threading of the push rod 407 within the entire injection process. During the dose setting step, user pushes the dialing cylinder 402 distally relative to the scale cylinder 403. Then, the locking engagement between 402b and 403c is disabled and the dialing cylinder 402 may be rotated relatively to the scale cylinder 403. After the dose setting, when there is absent of pushing force toward distal end of the automatic medication injection device 40, the dialing cylinder 402 is biased proximally and re-engaged with the scale cylinder 403, due to the resilient force generated by a separation spring 405. With reference to FIG. 38, before injection, the double ended needle 210 is assembled with the cartridge sheath 211 and the pre-filled cartridge 209. During injection, the push cap 401 is pushed toward to the distal end of the device, the releasable latch mechanism formed between hook feature 407a on the push rod 407 and the dialing cylinder 402 is released. The driving spring 406 drives the stopping ring 404 together with the push rod 407 to move toward the distal end of the automatic medication injection device 40. The piston 209a is pushed downward. The cartridge 209 and the double ended needle 210 also move downward due to the hydraulic resistance. Consequently, liquid medication in the pre-filled cartridge 209 is injected from the device into patient's body. The stopping ring 404 meets with the cartridge sheath 211. The first dose is delivered accordingly. During the re-setting or re-arming operation, the dialing cylinder 402 is pushed distally relative to the scale cylinder 403 in order to re-engage the dialing cylinder 402 with the push rod 404. During this re-arming, the separation spring 405 is compressed. With reference to FIG. 39, after the remove the distal toward force, the separation spring 405 pushes the dialing cylinder 402 and the push rod 407 back to the pre-injection position. A supporting spring 408 will push the cartridge sheath 211 and the cartridge 209 back to pre-injection position. Then, after setting another dose through locating the stopping ring to a more proximal location and assembling a new double ended needle, the device is ready for a subsequential injection.

Figure 40:
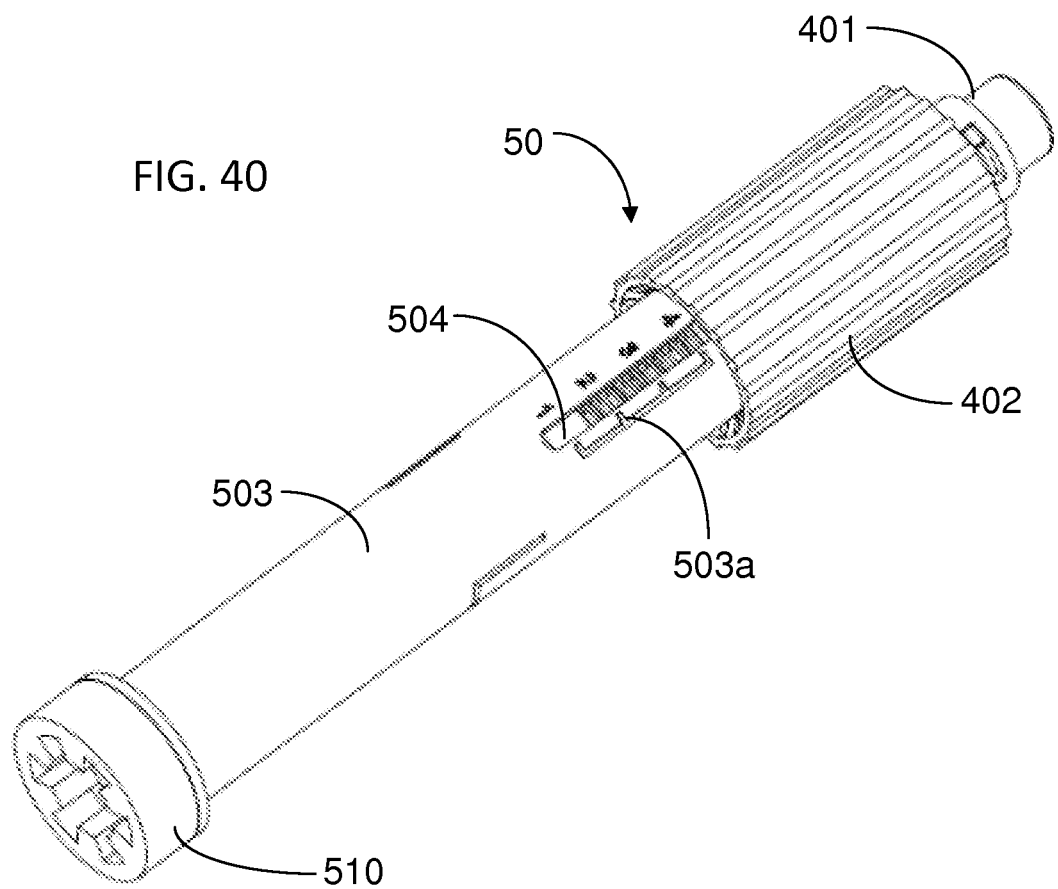
FIG. 40 is a perspective view of the fourth alternative automatic medication injection device assembly according to the invention.
Figure 41:
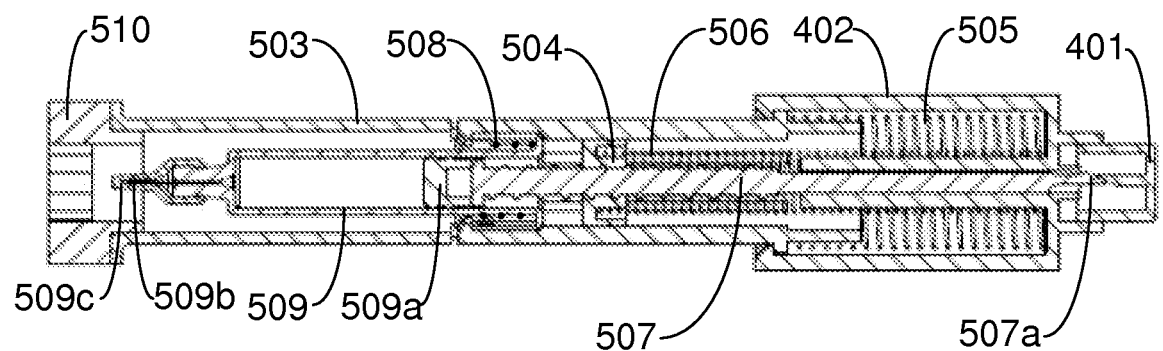
FIG. 41 shows a cross-sectional view of the fourth alternative automatic medication injection device assembly according to the invention.

FIGS. 40 and 41 illustrate the construction and function mechanism of the fourth alternative automatic medication injection device assembly 50 according to the invention. This exemplary automatic medication injection device assembly 50 has the same functional mechanisms as the automatic medication injection device assembly 40. Differently, a pre-filled syringe 509 is used as medication container. The pre-filled syringe 509 has a pierceable needle shield 509c. During the injection, user doesn't need to remove the needle shield 509c. The needle 509b can penetrate the needle shield 509c for medication injection. Compared with the automatic medication injection device assembly 40, in the automatic medication injection device assembly 50, separation spring 405 is changed to separation spring 505; driving spring 406 is changed to driving spring 506; push rod 407 is changed to push rod 507; supporting spring 408 is changed to supporting spring 508; and scale cylinder 403 is changed to scale cylinder 503. An end unit 510 can be used in a similar way to the end unit 104, during re-arming operation of the injection device.

All the features in the above embodiments and design concepts herein can be inter-changed and combined to generate new device designs. Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medical injection device having a distal end and a proximal end, comprising:
    a medication container having a movable piston;
    a push rod assembly displaceably disposed in said medical injection device, said push rod assembly having a plurality of spaced-apart position setting means disposed along the length thereof, said push rod assembly selectively displacing said movable piston to dispense a medicament from said medication container;
    a resilient member configured to bias said push rod assembly to move toward said distal end of said medical injection device;
    a releasable restraining member configured to releasably restrain said push rod assembly in a locked state against said biasing of said resilient member, wherein, upon release of said releasable restraining member, said push rod assembly moves under force of said resilient member toward said distal end of said medical injection device;
    an activation means configured to release said releasable restraining member; and
    a separation spring configured to move said push rod assembly toward said proximal end of said medical injection device.

2. A The medical injection device as in claim 1, wherein said medication container is a pre-filled syringe.

3. The medication injection device as in claim 2, wherein said pre-filled syringe has a luer lock connection.

4. The medical injection device as in claim 2, wherein said pre-filled syringe has a needle.

5. The medication injection device as in claim 4 further comprising an automatic needle insertion means comprising a driving spring and configured to automatically insert said needle into medication injection site.

6. The medication injection device as in claim 4 further comprising a pierceable needle shield.

7. The medication injection device as in claim 4 further comprising an end unit to cover said needle while said medical injection device is armed.

8. The medication injection device as in claim 1, wherein said medication container is a pre-filled cartridge.

9. The medication injection device as in claim 8 further comprising a cartridge sheath to host said pre-filled cartridge.

10. The medication injection device as in claim 8 further comprising a double ended needle.

11. The medication injection device as in claim 10 further comprising an automatic needle insertion means comprising a driving spring and configured to automatically insert said double ended needle into medication injection site.

12. The medication injection device as in claim 1, wherein said push rod assembly is extendable.

* * * * *